US009980799B2

(12) United States Patent
Wilson

(10) Patent No.: US 9,980,799 B2
(45) Date of Patent: May 29, 2018

(54) DENTAL APPLIANCE CASE

(71) Applicant: Wesley P. Wilson, Athens, AL (US)

(72) Inventor: Wesley P. Wilson, Athens, AL (US)

(73) Assignee: N CASE INC, Las Vegas, NV (US)

( * ) Notice: Subject to any disclaimer, the term of this patent is extended or adjusted under 35 U.S.C. 154(b) by 0 days. days.

(21) Appl. No.: 15/444,009

(22) Filed: Feb. 27, 2017

(65) Prior Publication Data

US 2017/0165041 A1 Jun. 15, 2017

Related U.S. Application Data

(63) Continuation of application No. 14/882,558, filed on Oct. 14, 2015.

(60) Provisional application No. 62/063,647, filed on Oct. 14, 2014.

(51) Int. Cl.
| | |
|---|---|
| *G08B 21/00* | (2006.01) |
| *A61C 19/02* | (2006.01) |
| *A61C 7/08* | (2006.01) |
| *A63B 71/08* | (2006.01) |
| *B65D 43/16* | (2006.01) |
| *A45D 44/20* | (2006.01) |
| *G08B 21/18* | (2006.01) |
| *H02J 7/02* | (2016.01) |

(52) U.S. Cl.
CPC .............. *A61C 19/02* (2013.01); *A45D 44/20* (2013.01); *A61C 7/08* (2013.01); *A63B 71/085* (2013.01); *B65D 43/163* (2013.01); *G08B 21/18* (2013.01); *H02J 7/025* (2013.01)

(58) Field of Classification Search
CPC .. A61C 19/02; A61C 7/08; A61C 7/00; A61C 13/00; A61C 2204/005; A61C 19/00; A61C 5/007; H02J 7/025; G08B 21/18; A45D 44/20; A63B 71/085; A63B 71/0036; B65D 43/163; A61F 5/566; A61B 5/682; A61B 5/4833
USPC .................... 340/540, 309.15, 568.1, 309.16; 206/205; 368/10
See application file for complete search history.

(56) References Cited

U.S. PATENT DOCUMENTS

| | | | | |
|---|---|---|---|---|
| 4,615,681 | A * | 10/1986 | Schwarz ............... | A24F 15/005 131/270 |
| 5,020,037 | A * | 5/1991 | Raven ................... | A61J 7/0481 221/2 |
| 6,417,761 | B1 * | 7/2002 | Elliott ...................... | A61C 7/00 128/859 |
| 2010/0102959 | A1 * | 4/2010 | Ashrafzadeh ........ | G06Q 10/087 340/540 |
| 2010/0164716 | A1 * | 7/2010 | Estevez ............... | G06F 19/3462 340/540 |

(Continued)

*Primary Examiner* — Anh V La
(74) *Attorney, Agent, or Firm* — Charmasson, Buchaca & Leach, LLP

(57) ABSTRACT

A dental appliance case for receiving a dental appliance is provided. In some embodiments, the case may include a power source, a sound device, an occupancy sensor, and a processing unit. The sound device may be configured to create an audible alert sound. The occupancy sensor may be operable to detect the presence of a dental appliance. The processing unit may be in electrical communication with the power source, occupancy sensor, and the sound device. The processing unit may be operable to operate the sound device to create an audible alert in response to an electronic communication from the occupancy sensor.

20 Claims, 8 Drawing Sheets

(56) References Cited

U.S. PATENT DOCUMENTS

2015/0320643 A1* 11/2015 Zhou .................... A61J 7/0418
  206/438

* cited by examiner

DENTAL APPLIANCE CASE

PRIOR APPLICATION

This is a continuation of U.S. patent application Ser. No. 14/882,558, filed 2015 Oct. 14, which claims the benefit of U.S. Provisional Utility Patent Application Ser. No. 62/063,647, filed 2014 Oct. 14, incorporated herein by reference.

FIELD OF THE INVENTION

This patent specification relates to the field of dental appliance cases. More specifically, this patent specification relates to dental appliance cases configured to provide information on a dental appliance.

BACKGROUND

Dental appliances are used for a variety of purposes and may include retainers, dentures, partial dentures, active aligners, protraction headgear, spring aligners, and the like. Users of these appliances face similar problems regardless of the type of appliance. Dental appliance users often face a problem of remembering to wear their appliance. By forgetting to wear a retainer, the user may encounter treatment setbacks such as their teeth shifting or not moving correctly requiring a lengthy and uncomfortable treatment period.

Users may also encounter the problem of remembering where they left their dental appliance. These appliances are usually expensive and difficult to replace. Much time and energy can be wasted on looking for lost appliances. If the appliance cannot be found, in addition to possible treatment setbacks, a user may be required to pay for a replacement appliance.

For dental appliances such as retainers, a user may have trouble remembering the amount of time they have been wearing their dental appliance each day. Without an accurate accounting of the amount of time the retainer has been worn, a user may also encounter treatment setbacks such as their teeth shifting or not moving correctly requiring a lengthy and uncomfortable treatment period.

Therefore, a need exists for novel apparatuses for reminding a user to wear their dental appliance. There also exists a need for novel apparatuses for preventing the loss of dental appliances. There is a further need for novel apparatuses for facilitating locating dental appliances. Finally, there exists a need for novel apparatuses for recording and reporting the amount of time a dental appliance is worn by a user.

SUMMARY

A dental appliance case is provided. In some embodiments, the case may comprise a power source, one or more alert devices, an occupancy sensor, and a processing unit. An alert device may comprise a light emitting diode, a sound device, and/or a vibration device. A sound device may be configured to create an audible alert such as an audible alert sound. A light emitting diode may be configured to create a visual alert such as an emission of light. A vibration device may be configured to create a tactile alert such as a vibration. The occupancy sensor may be operable to detect the presence of a dental appliance. The processing unit may be in electrical communication with the power source, occupancy sensor, and one or more alert devices. The processing unit may be operable to operate one or more alert devices to create an audible, visual, and/or tactile alert in response to an electronic communication from the occupancy sensor.

In some embodiments, the case may comprise a lid, a base, and a power source. The base and lid may be operable to be temporarily aligned and brought together, forming a cavity between the lid and base that is able to receive a power source, one or more alert devices, an occupancy sensor, and a processing unit. An occupancy sensor may be operable to detect the presence of a dental appliance. A processing unit may be in electrical communication with the power source, occupancy sensor, and one or more alert devices. The processing unit may be operable to operate one or more alert devices to create an audible, visual, and/or tactile alert in response to an electronic communication from the occupancy sensor.

In further embodiments, the case may comprise a lid, a base, and a power source. The base and lid may be operable to be temporarily aligned and brought together, forming a cavity between the lid and base that is able to receive a dental appliance. An occupancy sensor may be operable to detect the presence of a dental appliance in the cavity. An alert device may be configured to create an audible, visual, and/or tactile alert. A communication array may be operable to send and receive wireless communications. A processing unit may be in electrical communication with the power source, occupancy sensor, alert device, and the communication array. The processing unit may operate the alert device to create an audible, visual, and/or tactile alert and to operate the communication array to send wireless communications describing electronic communication from the occupancy sensor.

BRIEF DESCRIPTION OF THE DRAWINGS

Some embodiments of the present invention are illustrated as an example and are not limited by the figures of the accompanying drawings, in which like references may indicate similar elements and in which.

DESCRIPTION OF THE EXEMPLARY EMBODIMENTS

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1:
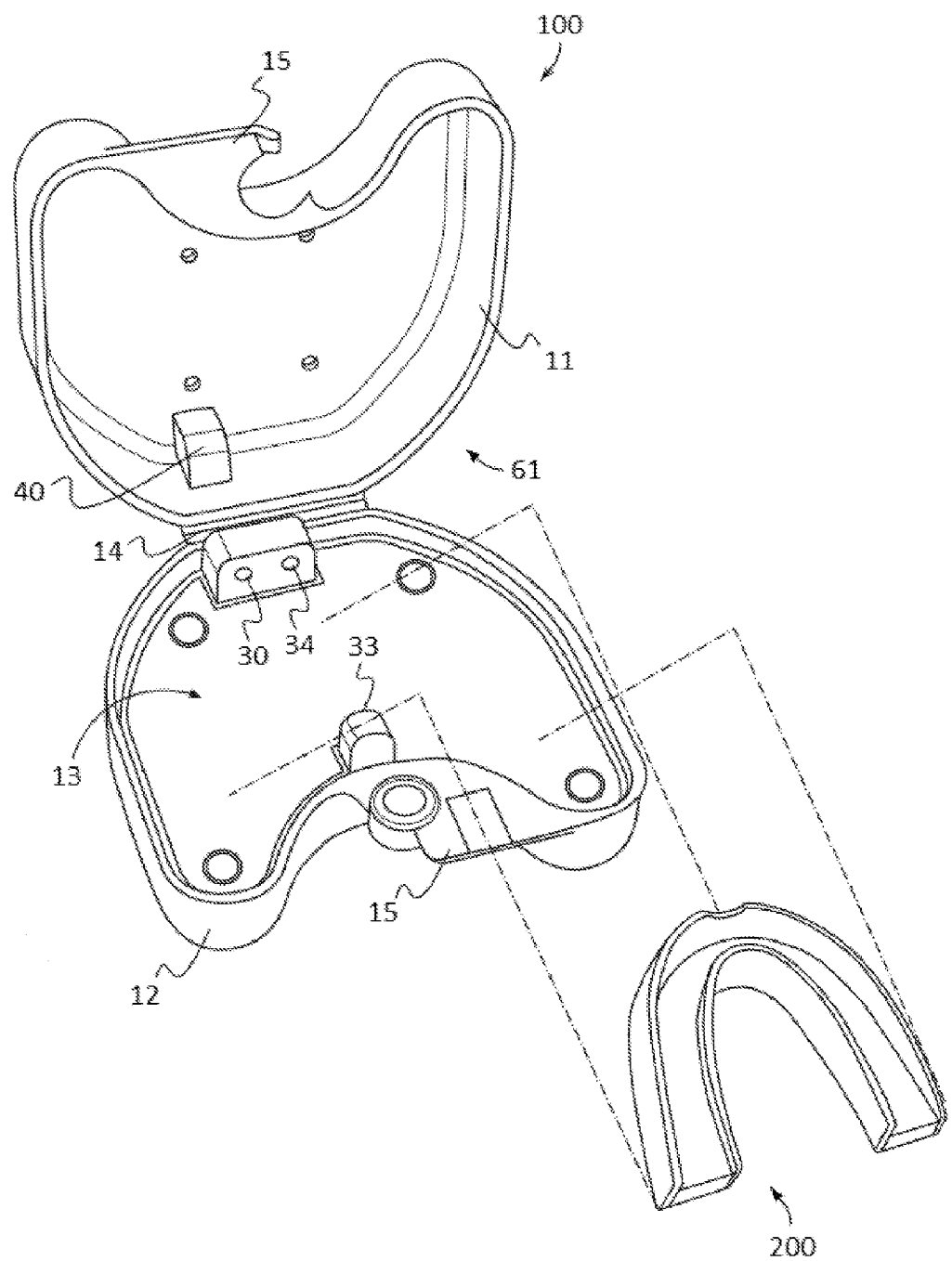
FIG. 1 depicts a top perspective view of an example of a dental appliance case in an open position showing insertion of a dental appliance into the dental appliance case according to various embodiments described herein.

For purposes of description herein, the terms "upper", "lower", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

New dental appliance cases are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

Figure 2:
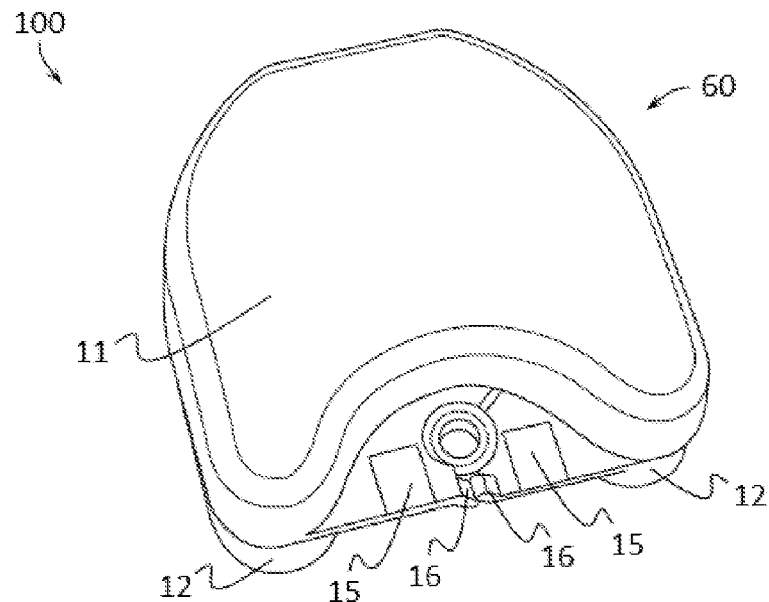
FIG. 2 illustrates a top perspective view of an example of a dental appliance case in a closed position according to various embodiments described herein.
Figure 3:
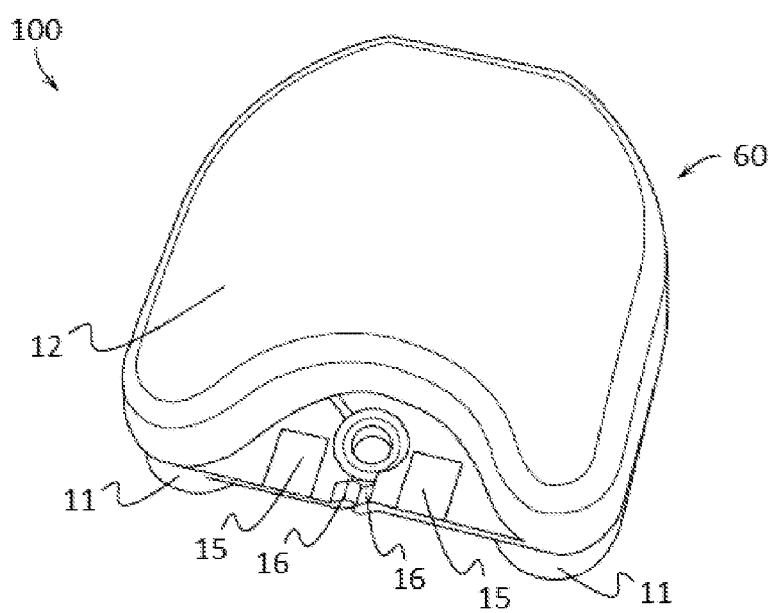
FIG. 3 shows a bottom perspective view of an example of a dental appliance case in a closed position according to various embodiments described herein.

The present invention will now be described by example and through referencing the appended figures representing preferred and alternative embodiments. FIGS. 1-3 depict an example of a dental appliance case ("the case") 100 according to various embodiments. In some embodiments, the case 100 may comprise a lid 11 and a base 12 which may be temporarily aligned and brought together as shown in FIGS. 2 and 3, to form a cavity 13 between the lid 11 and base 12 that is configured to receive a power source 36 (FIGS. 5-8), an occupancy sensor 32 (FIG. 8), a processing unit 21 (FIGS. 8 and 9), one or more alert devices 35, 38, 39 (FIGS. 7 and 8) and any other component of the case 100. In further embodiments, the case 100 may comprise a lid 11 and a base 12 which may be temporarily aligned and brought together as shown in FIGS. 2 and 3, to form a cavity 13 between the lid 11 and base 12 that is configured to receive a power source 36, an alert device 35, 38, 39, an occupancy sensor 32, a processing unit 21, any other component of the case 100, and a dental appliance 200 (FIG. 1). The cavity 13 may be configured to define a volume which is suitable for receiving a dental appliance 200 such as a retainer, mouth guard, or the like. In further embodiments, the case 100 may comprise an optional hinge 14 and an optional lid release 15 both providing an engagement with a base 12. A hinge 14 may pivotally couple a portion of the lid 11 to the base 12 while the lid release 15 may removably couple another portion of the lid 11 to the base 12. In still further embodiments, a lid 11 may comprise a lid release 15 and a base 12 may also comprise a lid release 15. When the lid 11 and base 12 are pivoted into a closed position 60 (FIGS. 2 and 3), a first lid release 15 may be removably coupled to a second lid release 15 and/or to a portion of the lid 11 and/or base 12 thereby closing off the cavity 13 and maintaining the case in a closed position 60. By uncoupling a first lid release 15 from a second lid release 15 and/or a portion of the lid 11 and/or base 12, portions of the lid 11 may be moved away from the base 12, such as by pivoting, thereby moving the case 100 into an open position 61 and granting access for insertion and removal of a dental appliance 200 to and from the cavity 13.

In some embodiments, a lid 11 and a base 12 may comprise a generally rectangular prism shape with rounded corners, and when aligned and brought together, form a cavity 13 (FIG. 3) or space between the two that is able to receive a retainer, denture, and other like dental appliances 200. In other embodiments, a cavity 13, lid 11 and/or a base 12 may be configured in a plurality of sizes and shapes including circular shaped, oval shaped, triangular shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes may be made without departing from the spirit or scope of the invention.

In some embodiments, one or more hinges 14 may be positioned anywhere on the case 100 to provide a pivotal joining engagement between the lid 11 and the base 12. A hinge 14 may comprise a butt hinge, butterfly hinge, flush hinge, barrel hinge, concealed hinge, continuous hinge, T-hinge, strap hinge, double-acting hinge, Soss hinge, a flexible material hinge, or any other type or style of hinge or pivotal joining method that allows portions of a lid 11 and base 12 to be pivoted away from each other. In further embodiments, a hinge 14 may comprise any type of hinge known in the art, including so-called "living" hinges, which typically comprise a linear, relatively flexible area between two relatively more rigid components, such as a line of thin plastic between thicker plastic portions, as is well known in the art. In some embodiments, a hinge 14 may comprise a spring or other tension providing device that is able to mechanically assist with the opening or closing of the lid 11. In other embodiments, a lid 11 and base 12 may be slidably joined together with a tongue and groove engagement allowing portions of a lid 11 to be slid open and closed from the base 12. In further embodiments, a lid 11 and base 12 may be joined with any other type of engagement that allows a portion of a lid 11 to be moved towards and away from a base 12 thereby restricting and granting access to the cavity 13 of the case 100.

In some embodiments, one or more lid releases 15 may be positioned anywhere on the case 100 that are configured to temporarily allow or deny a portion of a lid 11 from moving with respect to the base 12 by temporarily engaging a portion of the lid 11 to the base 12. In further embodiments, a lid release 15 may comprise a pressure catch 16 that may be configured to secure or engage a portion of the lid 11 to the base 12 when a portion of the lid 11 is pressed against the base 12 and/or lid release 15 such as when the case 100 is in a closed position 60 (FIGS. 2 and 3). By pressing on the lid release 15, when the case 100 is in a closed position 60, the pressure catch 16 may be released allowing portions of the lid 11 to move away from the base 12 allowing the base to be in an open position 61 as shown in FIG. 1. In other embodiments, a lid release 15 may be configured to temporarily join or engage a portion of a lid 11 to a base 12 with a clasp type connection method, magnetic lock type connection method, key lock type connection method, electronic lock type connection method, combination lock type connection method, push-to-lock type connection method, a turn-to-lock type connection method, slide-to-lock type connection method or any other suitable temporary connection method as one reasonably skilled in the art could envision to serve the same function.

As shown in the example of FIG. 1, the case 100 is illustrated in an open position 61 with a portion of the lid 11 pivoted away from the base 12 while still being engaged together at a hinge 14. The cavity 13 formed between the base 12 and lid 11 is configured to receive and secure a retainer, denture, or other like dental appliance 200. In some embodiments, the case 100 may comprise a floor 18 which may be configured to separate electronic components of the case 100 from a dental appliance 200 received in the cavity 13. In some embodiments, a floor 18 may be joined to or coupled to the base 12 with electronic components stored between the floor 18 and the base 12. In other embodiments, a floor 18 may be joined to or coupled to the lid 11 with electronic components stored between the lid 11 and the floor 18. In further embodiments, a floor 18 may be joined or coupled to the base 12 and/or lid 11 with electronic components stored between the lid 11 and the floor 18 and/or the base 12 and the floor 18. A floor 18 may be joined or coupled to a lid 11 or base 12 to prevent fluids and debris associated with a dental appliance 200 received in the cavity 13 from reaching the electronic components of the case 100.

Figure 4:
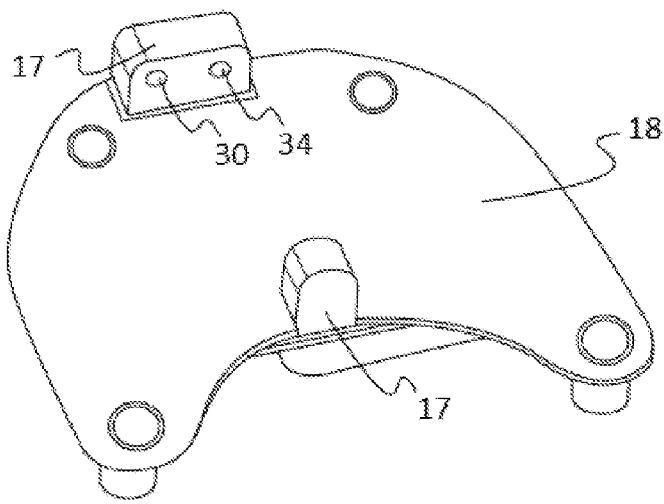
FIG. 4 depicts a top perspective view of an example of a floor according to various embodiments described herein.

FIG. 4 depicts a top perspective view of an example of a floor 18 according to various embodiments described herein. In some embodiments, a floor 18 may comprise or be coupled to one or more electronic components such as a lid sensor 30, a control input 31, and/or an occupancy sensor 32 (FIG. 8) which may include a sensor receiver 34, and/or a sensor emitter 33. In preferred embodiments, electronic components of the floor 18 and/or coupled to the floor 18 may be water proof and may be in electrical communication with other electronic components located or stored between the lid 11 and the floor 18 and/or the base 12 and the floor 18. Optionally, one or more sensor housings 17 may be coupled to the floor 18 to provide structures for one or more sensors and other electronic components to be positioned on or within. In some embodiments, a sensor emitter 33 may be coupled in a first sensor housing 17 and a sensor receiver 34 may be coupled within a second sensor housing 17. The sensors 33, 34, may use infrared light to detect if a dental appliance 200 (FIG. 1) is within the cavity 13 (FIG. 1) such as by detecting if the dental appliance interrupts the infrared light. By disposing the sensors 33, 34, within the sensor housings 17, the sensor housings 17 may act as infrared light and sensor shields.

In some embodiments, a case 100 may comprise an occupancy sensor 32 (FIG. 8) which may include a sensor receiver 34 and/or a sensor emitter 33 which are configured to detect a dental appliance 200 (FIG. 1). The sensor receiver 34 may comprise an infrared light receiver or detector and a sensor emitter 33 may comprise an infrared light emitter. In further embodiments, a dental appliance 200 placed proximate to a sensor receiver 34 and/or a sensor emitter 33, such as in the cavity 13, may be detected as it interrupts the path of infrared light between an infrared sensor emitter 33 and an infrared sensor receiver 34. When the infrared light is not interrupted, the infrared sensor receiver 34 and infrared sensor emitter 33 may be used to detect that a dental appliance 200 is not proximate to a sensor receiver 34 and/or a sensor emitter 33, such as not in the cavity 13.

Figure 5:
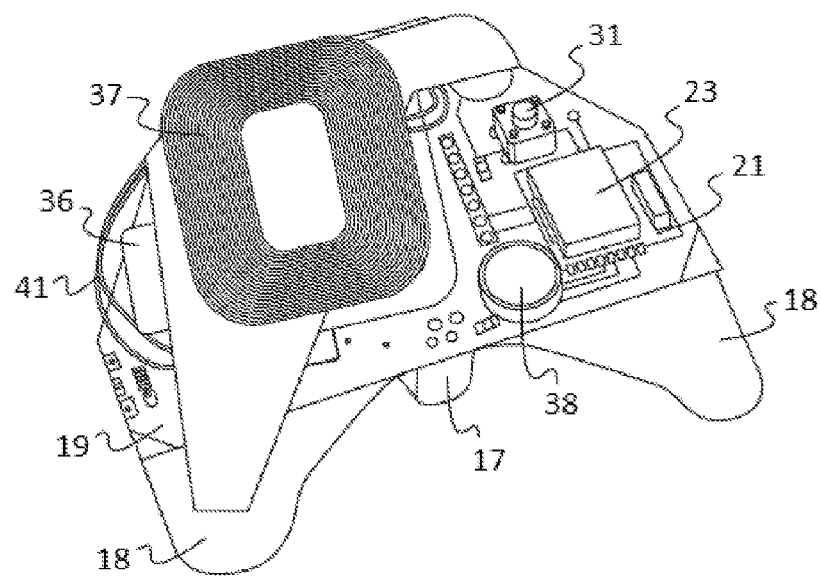
FIG. 5 illustrates a bottom perspective view of an example of a floor assembled with some components of a dental appliance case according to various embodiments described herein.
Figure 6:
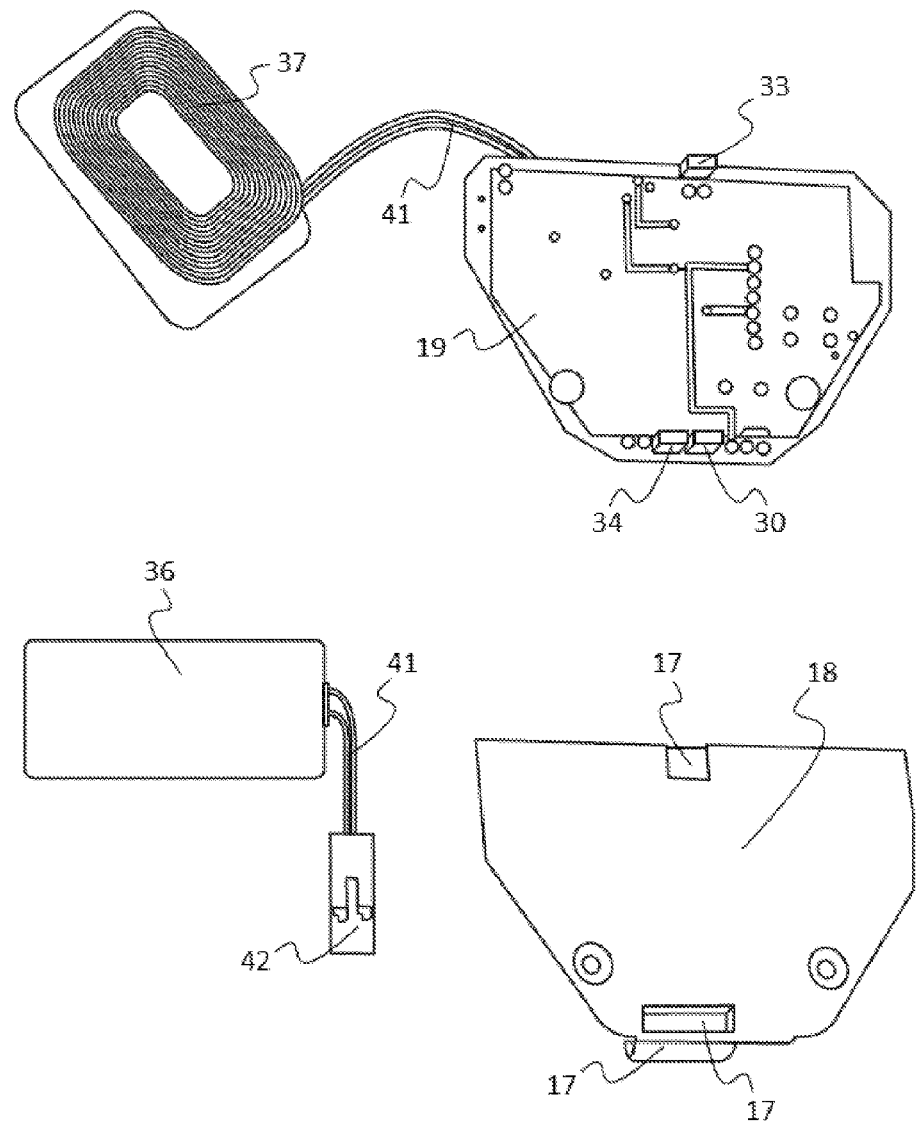
FIG. 6 shows a perspective exploded top view some of the components of a dental appliance case according to various embodiments described herein.
Figure 7:
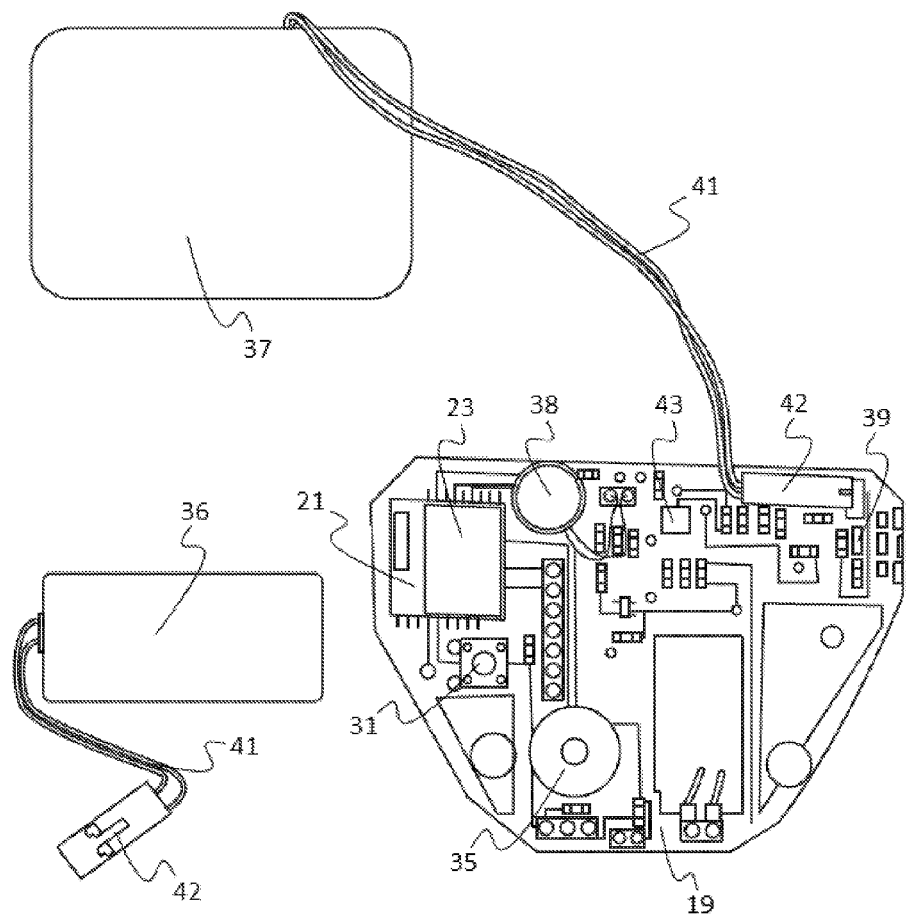
FIG. 7 depicts a perspective exploded bottom view some of the components of a dental appliance case according to various embodiments described herein.
Figure 8:
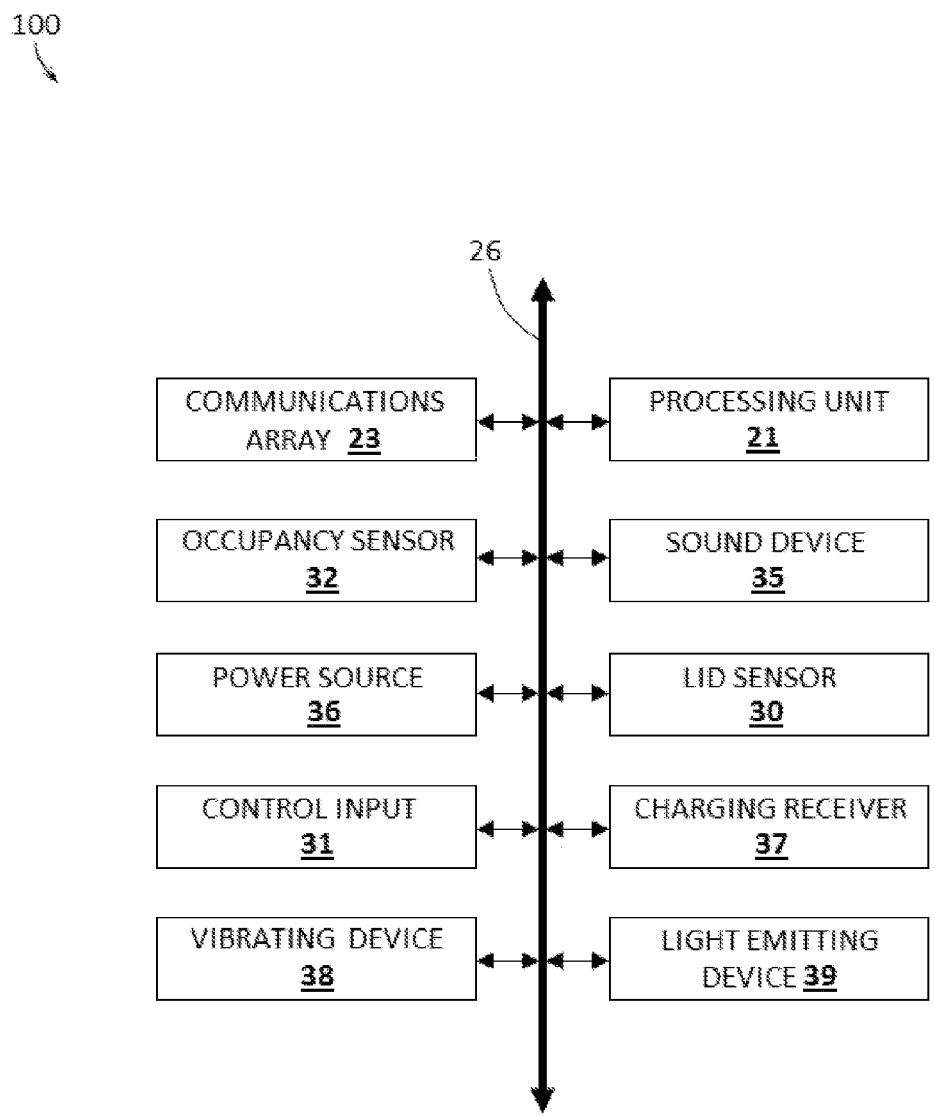
FIG. 8 illustrates a block diagram of some of the components of a dental appliance case according to various embodiments described herein.

FIGS. 5-7 illustrate examples of some electronic components of a dental appliance case 100 and some optional configurations that they may be assembled in, while FIG. 8 illustrates a block diagram of some of the electronic components of a case 100 according to various embodiments described herein. In some embodiments, a case 100 may comprise a circuit board 19 which may be positioned between a base 12 and a floor 18. In other embodiments, a circuit board 19 may be positioned between a lid 11 and a floor 18. A circuit board 19 may comprise and/or provide electrical communication between one or more electronic components such as a processing unit 21, a lid sensor 30, a control input 31, a sensor receiver 34, a sensor emitter 33, an alert device 35, 38, 39 and/or a communications array 23. In further embodiments, a circuit board 19 may comprise a local bus 26 which may provide electrical communication between one or more electronic components.

In some embodiments, a circuit board 19 may comprise a printed circuit board (PCB) which mechanically supports and electrically connects electronic components using conductive tracks, pads and other features etched from copper sheets laminated onto a nonconductive substrate. PCBs can be single sided (one copper layer), double sided (two copper layers) or multi-layer. Conductors on different layers may be connected with plated-through holes called vias. In some embodiments, a circuit board 19 may only comprise copper connections and no embedded components and may be called a printed wiring board (PWB) or etched wiring board. In other embodiments, a circuit board 19 may comprise a printed circuit assembly (PCA), printed circuit board assembly or PCB assembly (PCBA), a circuit card assembly (CCA), or a backplane assembly, or any other suitable electrical connection and communication method including standard wiring and the like.

In some embodiments, a case 100 may comprise a lid sensor 30 such as a magnetic sensor that is operable to detect if the lid 11 is open, closed, and/or optionally partially opened or closed. In further embodiments, a lid sensor 30 may comprise a Hall effect sensor which may be positioned on the floor 18, base 12, and/or lid 11 and which may detect increases or decreases, and therefore proximity, in an electric field generated by the magnetic material of a magnet 40 (FIG. 1) which may be complementarily positioned on the floor 18, base 12, and/or lid 11 to detect if the lid 11 is open, closed, and/or partially opened or closed. In other embodiments, a lid sensor 30 may comprise a pressure switch, an electrical circuit, or any other method configured to detect if the lid is open, closed, or optionally not open or closed. In further embodiments, a case 100 may comprise a reed switch, a pressure sensor, a contact sensor, a button mount, an ambient light sensor, or any other suitable sensor to detect if the lid 11 is open, closed, or partially opened or closed.

In some embodiments, a case 100 may comprise a control input 31 which may be configured to control a function of an electronic component. In further embodiments, a control input 31 may comprise an input such as turnable control knobs, depressable button type switches, slide type switches, rocker type switches, or any other suitable input that may be used to modulate electricity between one or more electronic components of the case 100 to control a function of the case 100.

In some embodiments, a case 100 may comprise an occupancy sensor 32 which may include a sensor receiver 34 and/or a sensor emitter 33 which are configured to detect if a dental appliance 200 (FIG. 1) is in the cavity 13. In further embodiments, an occupancy sensor 32 may comprise an RFID sensor receiver, a magnetic sensor receiver, an Ultraviolet light receiver, an optical receiver, or any other sensor receiver that may be used to detect the presence or absence of a dental appliance 200 in a cavity 13. In still further embodiments, an occupancy sensor 32 may comprise a RFID emitter, a magnetic field generating material such as magnetic metals and permanent magnets, an Ultraviolet light emitter, an optical light emitter or any other sensor receiver that may be used to detect the presence or absence of a dental appliance 200 in a cavity 13. In even further embodiments, a case 100 may comprise a reed switch, a button mount, a force sensor, an ambient light sensor, or any other suitable sensor to detect the presence or absence of a dental appliance 200 in a cavity 13.

In some embodiments, a case 100 may comprise a power source 36, such as a rechargeable and/or replaceable battery, which may provide electrical power to the electronic components of the case 100. A power source 36 may be positioned anywhere in the case 100 such as between the floor 18 and the base 12 (FIGS. 1-3). One or more wires 41, electrical clips 42, or other electrical couplings may provide electrical communication between the power source 36 a circuit board 19 or local bus 26. In further embodiments, a case 100 may comprise a charging receiver 37 which may be in electrical communication with a power source 36 such as a rechargeable battery. One or more wires 41, electrical clips 42, or other electrical couplings may also provide electrical communication between a charging receiver 37 and the power source 36, circuit board 19, and/or local bus 26. In still further embodiments, a charging receiver 37 may comprise a wireless charging receiver, such as a Qi Standard Wireless charging Receiver or any other inductive charging or wireless power receiver, which may be configured to receive energy through an inductive coupling and to electrically communicate the energy to the power source 36 or a power management microchip 43 in electronic communication with the charging receiver 37 allowing wireless energy to inductively charge the power source 36. In still further embodiments, a charging receiver 37 may comprise an electrical connector such as a USB connector such as a micro-USB, mini-USB, Type A USB plug, Type B USB plug, Mini-A USB plug, Mini-B USB plug, Micro-A USB plug, Micro-B USB plug, Micro-B USB 3.0 plug, ExtMicro USB plug, Lightning plug, 30-pin dock connector, Pop-Port connector, Thunderbolt plug, Firewire plug, Portable Digital Media Interface (PDMI) plug, coaxial power connector plug, barrel connector plug, concentric barrel connector plug, tip connector plug, or any other plug, connector, or receptacle capable of electrical communication.

In some embodiments, a case 100 may comprise one or more alert devices such as one or more sound devices 35 which may comprise a speaker which may be operable to produce or create one or more audible alert sounds at one or more volume levels. In further embodiments, a sound device 35 may comprise a buzzer, a piezoelectric sound producing device, a dielectric elastomer sound producing device, a buzzer, a moving coil loudspeaker, an electrostatic loudspeaker, an isodynamic loudspeaker, a piezo-electric loudspeaker, or any other device capable of producing one or more sounds. In further embodiments, a case 100 may comprise one or more alert devices such as one or more vibration devices 38, light emitting devices 39, and/or a sound devices 35 configured to relay haptic, visual, and/or auditory alert information from a case 100 to a user. A light emitting device 39 may include a light emitting diode (LED), incandescent light bulb, halogen light bulb, laser light emitter, electroluminescent light source, neon light source, or any other suitable light source which is able to emit light, such as constant on light or intermittent light in one or more colors and/or intensities, viewable by a user as an alert.

In some embodiments, a case 100 may comprise one or more alert devices such as one or more vibrating devices 38 configured to produce vibrations. In further embodiments, a vibrating device 38 may comprise a long life brushless (BLDC) vibration motor, a coin or pancake vibration motor, an encapsulated vibration motor, an enclosed vibration motor, a pager motor, an eccentric rotating mass (ERM) motor, a linear resonant actuator (LRA), a printed circuit board (PCB) mounted vibration motor, or any other electrical device capable of producing vibrations.

In some embodiments, a case 100 may comprise a communications array 23 which is operable to send and receive wireless and/or wired communications. In further embodiments, a communications array 23 may comprise a Bluetooth receiver and transmitter and which enables wireless communication to a network or an external access client device (FIG. 10) such as cell phones, smart phones 300A, tablet computers, laptop computers 300B, wearable computers such as watches, Google Glasses, etc. and the like. In other embodiments, a communications array 23 may comprise a receiver and transmitter which enables any number of suitable wireless data communication protocols, techniques, or methodologies including, without limitation: RF; IrDA (infrared); Bluetooth; Wifi; ZigBee (and other variants of the IEEE 802.15 protocol); IEEE 802.11 (any variation); IEEE 802.16 (WiMAX or any other variation); Direct Sequence Spread Spectrum; Near-Field Communication (NFC); Frequency Hopping Spread Spectrum; Long Term Evolution (LTE); cellular/wireless/cordless telecommunication protocols (e.g. 3G/4G, etc.); iBeacon; wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication.

Figure 9:
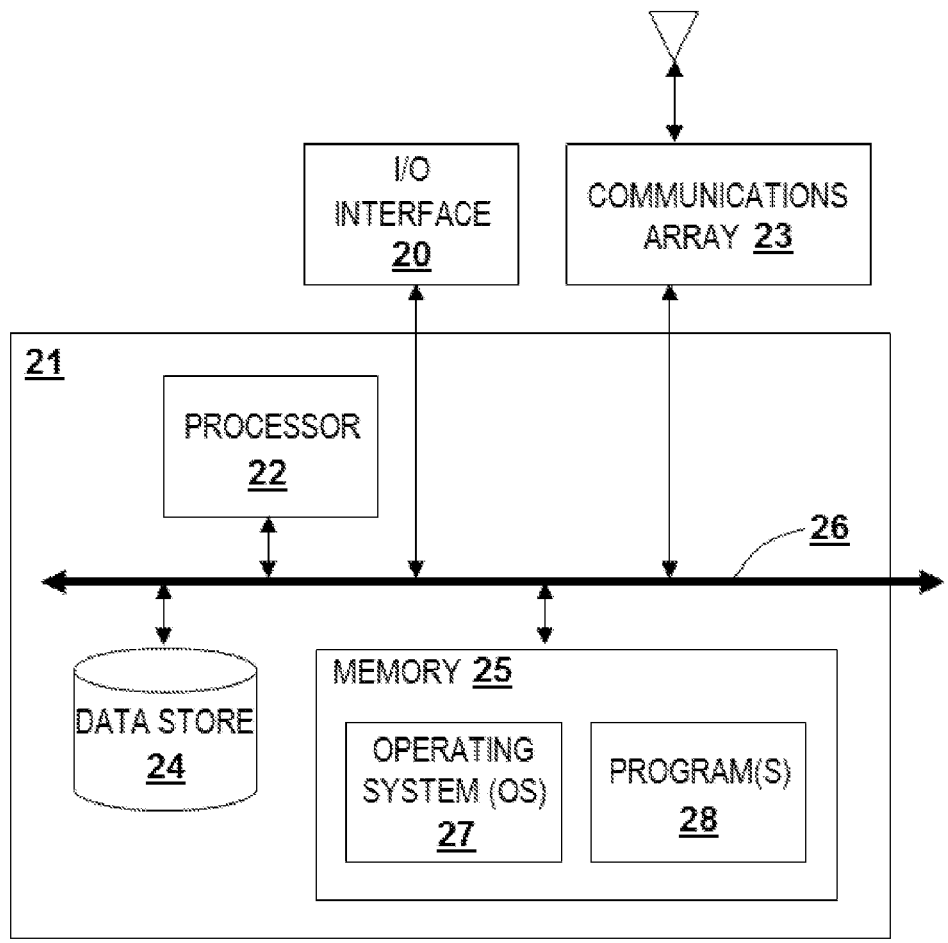
FIG. 9 shows a block diagram of some of the components of a processing unit according to various embodiments described herein.

FIG. 9 shows a block diagram of some of the components of a processing unit 21 according to various embodiments described herein. In some embodiments, a processing unit 21 may comprise a small computer on a single integrated circuit typically used for embedded applications and preferably comprising a processor core, memory, and programmable input/output peripherals. Program memory in the form of NOR flash or OTP ROM may also be included on chip, as well as a typically small amount of RAM. A processing unit 21 may be used to receive input from, control, or modulate one or more of the functions of any electronic component of the case 100.

The processing unit 21 may be configured to trigger one or more alerts or notifications which may be produced by a component of the case 100 in response to an electronic communication from a communications array 23, an occupancy sensor 32, a lid sensor 30, a power source 36, and/or a control input 31. An alert may include audible, tactile, and visual alerts. In some embodiments, a processing unit 21 may be configured to produce an audible alert by operating a sound device 35 to produce or create one or more audible sounds at one or more volume levels. In some embodiments, a processing unit 21 may be configured to produce a tactile alert by operating a sound device 35 to produce or create one or more vibrations which may vibrate the case 100 to produce a tactile alert perceptible by touch. In some embodiments, a processing unit 21 may be configured to produce a visual alert by operating a light emitting device 39 or any other type of light emitting element to produce or create one or more colors of light at one or more brightness intensities which may illuminate to produce a visual alert.

In further embodiments, a processing unit 21 may be a digital device that, in terms of hardware architecture, generally includes a processor 22, a data store 24, and memory 25. The processing unit 21 may be in electrical communication with a communications array 23 and one or more input/output (I/O) interfaces 20, such as a lid sensor 30, control input 31, occupancy sensor 32, sensor receiver 34, sensor emitter 33, sound device 35, power source 36, charging receiver 37, a vibration device 38, and/or a light emitting device 39. It should be appreciated by those of ordinary skill in the art that FIG. 9 depicts the processing unit 21 in an oversimplified manner, and a practical embodiment may include additional components and suitably configured processing logic to support known or conventional operating features that are not described in detail herein.

The components (22, 23, 24, 25, 27, 28, and 30) are communicatively coupled via a local interface 26. The local interface 26 can be, for example but not limited to, one or more buses or other wired or wireless connections, as is known in the art. The local interface 26 can have additional elements, which are omitted for simplicity, such as controllers, buffers (caches), drivers, repeaters, and receivers, among many others, to enable communications. Further, the local interface 26 may include address, control, and/or data connections to enable appropriate communications among the aforementioned components.

The processor 22 is a hardware device for executing software instructions. The processor 22 can be any custom made or commercially available processor, a central processing unit (CPU), an auxiliary processor among several processors associated with the processing unit 21, a semiconductor-based microprocessor (in the form of a microchip or chip set), or generally any device for executing software instructions. When the processing unit 21 is in operation, the processor 22 is configured to execute software stored within the memory 25, to communicate data to and from the memory 25, and to generally control operations of the processing unit 21 pursuant to the software instructions. In an exemplary embodiment, the processor 22 may include a mobile optimized processor such as optimized for power consumption and mobile applications.

The I/O interfaces 20 may include any other electronic component of the case 100, such as a lid sensor 30, control input 31, occupancy sensor 32, sensor receiver 34, sensor emitter 33, sound device 35, power source 36, charging receiver 37, a vibration device 38, and/or a light emitting device 39 may be used to receive input from and/or for providing output from the case 100. Input can be provided via, for example, a lid sensor 30, control input 31, occupancy sensor 32, sensor receiver 34, sensor emitter 33, and/or charging receiver 37. System output can be provided via a communications array 23, a light emitting device 39, a vibration device 38, and/or a sound device 35. The I/O interfaces 20 can also include, for example, a charging indicator light emitting device 39 or any other type of light emitting device which may be positioned anywhere on the case 100, a serial port, a parallel port, a small computer system interface (SCSI), an infrared (IR) interface, a radio frequency (RF) interface, a universal serial bus (USB) interface, and the like. The I/O interfaces 20 can include a graphical user interface (GUI) that enables a user to interact with the processing unit 21. Additionally, the I/O interfaces 20 may further include an imaging device, i.e. camera, video camera, etc.

The memory 25 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 25 may incorporate electronic, magnetic, optical, and/or other types of storage media. Note that the memory 25 may have a distributed architecture, where various components are situated remotely from one another, but can be accessed by the processor 22. The software in memory 25 can include one or more software programs, each of which includes an ordered listing of executable instructions for implementing logical functions. In the example of FIG. 9, the software in the memory 25 includes a suitable operating system (O/S) 27 and programs 28. The operating system 27 essentially controls the execution of other computer programs, and provides scheduling, input-output control, file and data management, memory management, and communication control and related services. The programs 28 may include various applications, add-ons, etc. configured to provide end user functionality with the processing unit 21. For example, exemplary programs 28 may include, but not limited to, a clock or timer program which may be configured to track input form an I/O interface 20 and to correlate the input with a time stamp or time period. In a typical example, the end user typically uses one or more of the programs 28 to control the functions of the electronic components of the case 100.

Figure 10:
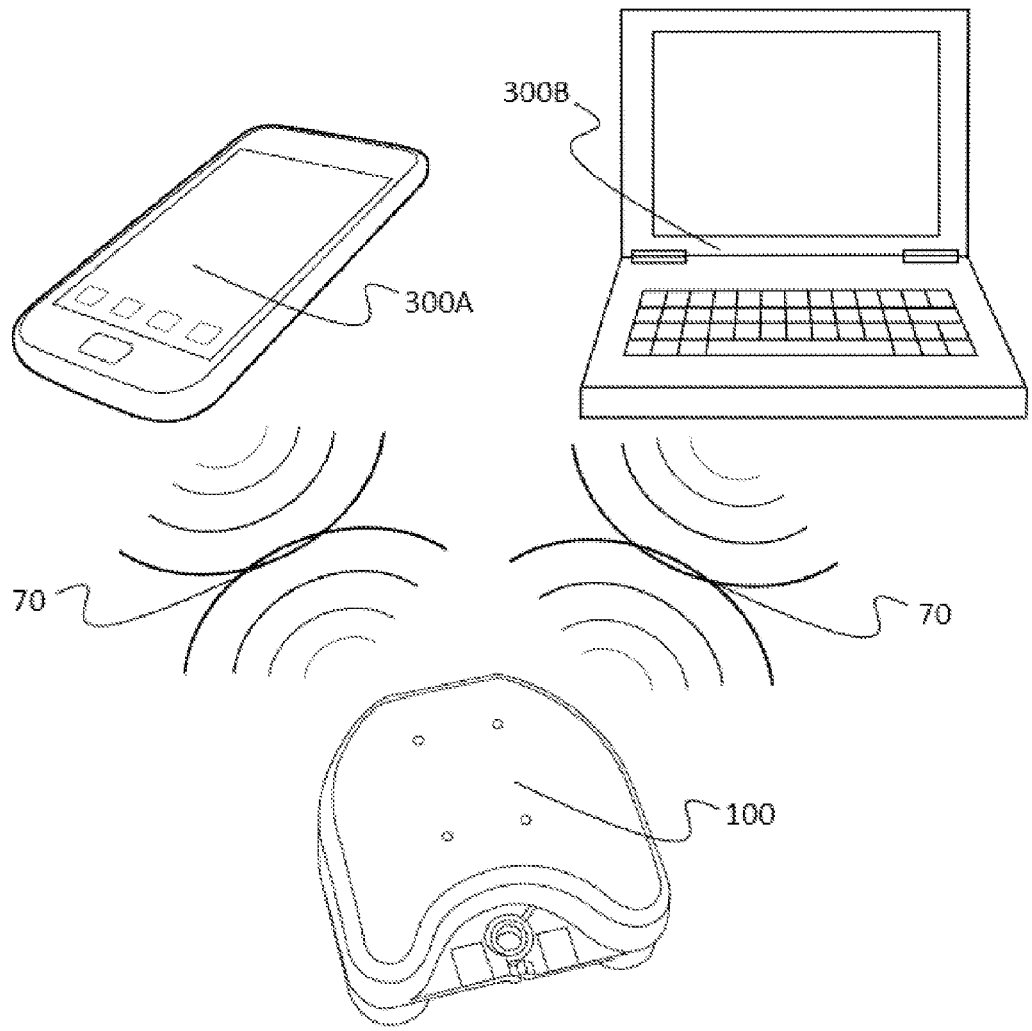
FIG. 10 depicts a perspective view of an example of a dental appliance case in wireless communication with client devices according to various embodiments described herein.

FIG. 10 depicts a perspective view of an example of a dental appliance case 100 in wireless communication 70 with client devices according to various embodiments described herein. In some embodiments, a processing unit 21 and communications array 23 may be used to record and process input from a lid sensor 30, occupancy sensor 32, or any other sensor and to communicate the input to one or more external access client devices such as cell phones, smart phones 300A, computers 300B, such as tablet computers, laptop computers, wearable computers, and the like. In some embodiments, a processing unit 21 and communications array 23 may communicate the input directly to external access client 300A, 300B, devices through Bluetooth, Wifi, NFC, or other wireless communications, thereby triggering a notification such as a text message, email message, push notification, application notification, and the like on an external access client device. In other embodiments, a processing unit 21 and communications array 23 may communicate the input over a network to external access client devices 300A, 300B, through Wifi, cellular communications, or other wireless communications, thereby triggering a notification such as a text message, email message, push notification, application notification, and the like on an external access client device 300A, 300B. In further embodiments, a processing unit 21 and communications array 23 may communicate the input directly to external access client devices 300A, 300B, and/or communicate the input over a network to external access client devices 300A, 300B, through Wifi, cellular communications, or other wireless communications, thereby triggering a notification such as a text message, email message, push notification, application notification, and the like on an external access client device 300A, 300B. In still further embodiments, a processing unit 21 and communications array 23 may be in wired communication with an external access client devices 300A, 300B, and the processing unit 21 may communicate the input directly to external access client devices 300A, 300B, thereby triggering a notification such as a text message, email message, push notification, application notification, and the like on an external access client device 300A, 300B.

In some embodiments, the communications array 23 may be in wireless communication with an external access client device 300A, 300B, and when the wireless communication is broken, the processing unit 21 may trigger an audio, visual, and/or tactile alert. For example, the communications array 23 may be in Bluetooth wireless communication with the smart phone device 300A of a user. If the user, with their smart phone device 300A, forgets and leaves the case 100 behind, the wireless communication may be broken as the distance between the case 100 and the smart phone device 300A becomes too great for Bluetooth communication. Once the wireless communication is broken, the processing unit 21 may trigger an alert, such as a sound from the sound device 35, a vibration from a vibration device 38, or a light from the light emitting device 39. In still further embodiments, as the distance between the case 100 and the smart phone device 300A approaches a distance too great for Bluetooth communication, the communication array may send a wireless communication to the smart phone device 300A and the smart phone device 300A may produce an alert.

The processing unit 21 may comprise a clock or timer program 28 (FIG. 9) which may record the time of a sensor event, the time between sensor events, or any other temporal parameter. The processing unit 21 may be configured to operate the communications array 23, sound device 35, a vibration device 38, and/or a light emitting device 39 based on the temporal data provided by the clock or timer program 28 and based on sensor data received or not received allowing the case to audibly, visually, vibrationally, and/or wirelessly communicate the temporal and/or sensor data.

In some embodiments, the microcontroller 21 may operate the communications array 23, light emitting device 39, sound device 35, and/or a vibration device 38 after receiving or not receiving input from a lid sensor 30. For example, the processing unit 21 may or may not receive input from a lid sensor 30 for a period of time or at a certain time such as a user bed time. If the lid sensor 30 does not detect that the lid has been opened or otherwise operated, the processing unit 21 may operate the communications array 23 to send a wireless electronic communication to an external access client device 300A, 300B, such as with a Bluetooth or WiFi wireless communication to notify a user that the lid 11 has not been opened for a period of time or at a certain time. In further embodiments, a processing unit 21 may receive input from a lid sensor 30 or any other sensor detecting if and when a dental appliance is in the cavity 13 or if and when the lid 11 has been opened, and the processing unit 21 may operate the sound device 35 to produce an audible sound, and/or operate the vibration device 38 to produce vibrations to notify a user of the sensor input, and/or a light emitting device 39 to emit light for a visual alert.

In some embodiments, the microcontroller 21 may operate the communications array 23, sound device 35, light emitting device 39, and/or a vibration device 38 after receiving or not receiving input from an occupancy sensor 32. For example, the processing unit 21 may receive input from an occupancy sensor 32 that a dental appliance 200 is detected, such as by being in the cavity 13, for a period of time. Once the period of time meets or exceeds a threshold, such as meeting or exceeding the period of time for a user to eat a meal, the processing unit 21 may operate a communications array 23. After a dental appliance 200 is detected, such as by being in the cavity 13, for a period of time, the processing unit 21 may operate the communications array 23 to send a wireless electronic communication to an external access client device 300A, 300B, such as with a Bluetooth or WiFi wireless communication to notify a user of the sensor input. Likewise, after the dental appliance 200 is detected, such as by being in the cavity 13, for a period of time, the processing unit 21 may operate the sound device 35 to produce an audible sound, and/or operate the vibration device 38 to produce vibrations to notify a user of the sensor input, and/or operate the light emitting device 39 to produce a visual alert. In another example, the processing unit 21 may receive input from an occupancy sensor 32 that a dental appliance 200 is detected, such as by being in the cavity 13, for a period of time such as a sleep period when the user should be wearing the dental appliance. If the dental appliance 200 is detected, such as by being in the cavity 13, during the sleep time period, such as between 10 PM and 6 AM, the processing unit 21 may operate the communications array 23, sound device 35, a vibration device 38, and/or a light emitting device 39, when the dental appliance 200 is detected, such as by being in the cavity 13, during the 10 PM and 6 AM time period.

In some embodiments, the microcontroller 21 may operate the sound device 35, light emitting device 39, and/or a vibration device 38 after receiving or not receiving input from the communications array 23. For example, an external access client device 300A, 300B, may be in wireless communication with the communications array 23 of the case 100. Upon receiving a certain wireless communication or command from the client device 300A, 300B, the processing unit 21 may operate the sound device 35 to produce an audible alert sound, a light emitting device 39 to emit light for a visual alert, and/or operate the vibration device 38 to produce alert vibrations to notify a user of the location of the case 100. In another example, if the wireless communication with the communications array 23 does not receive a wireless communication from an external access client device 300A, 300B, such as within a certain period of time, the processing unit 21 may operate the sound device 35 to produce an audible alert sound, a light emitting device 39 to emit light for a visual alert, and/or operate the vibration device 38 to produce alert vibrations to notify a user of the location of the case 100.

In other preferred embodiments, a processing unit 21 may receive input from a wireless communications array 26, an occupancy sensor 32, lid sensor 30, and/or any other sensor detecting if a dental appliance 200 is in the case 100 and may notify a user by sending a push notification such as a text message, email message, and the like to a client device 300A, 300B. In still further embodiments, a processing unit 21 may receive input from an occupancy sensor 32, lid sensor 30, or any other sensor detecting how much time and at what times a dental appliance 200 is in or out of a case 100. In even further embodiments, a processing unit 21 and communications array 23 may communicate the location of the case 100 and/or give the proximity of the case 100 to a client device 300A, 300B.

While some materials have been provided, in other embodiments, the elements that comprise the case 100 such as the lid 11, base 12, electronic components 19, 20, 21, 22, 23, 25, optional hinge 14, optional lid release 15, optional pressure catch 16, and/or optional floor 18 may be made from durable materials such as aluminum, steel, other metals and metal alloys, wood, hard rubbers, hard plastics, fiber reinforced plastics, carbon fiber, fiber glass, resins, polymers or any other suitable materials including combinations of materials. Additionally, one or more elements may be made from or comprise durable and slightly flexible materials such as soft plastics, silicone, soft rubbers, or any other suitable materials including combinations of materials. In some embodiments, one or more of the elements that comprise the case 100 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the case 100 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, slide-to-lock type connection method or any other suitable temporary connection method as one reasonably skilled in the art could envision to serve the same function. In further embodiments, one or more of the elements that comprise the case 100 may be coupled by being one of connected to and integrally formed with another element of the case 100.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A dental appliance case, the case comprising:
   a lid;
   a base having an open cavity that is able to at least partially receive a dental appliance, wherein the base and lid are operable to be temporarily aligned and brought together to form a closed cavity between the lid and base that is able to fully receive the dental appliance;
   a power source;
   an alert device configured to create an alert, wherein the alert device is selected from the group consisting of a sound device, a vibration device, and a light emitting device;
   an occupancy sensor, wherein the occupancy sensor is operable to detect the presence of the dental appliance within the open cavity, regardless of whether the lid and base are brought together; and,
   a processing unit in electrical communication with the power source, occupancy sensor, and the alert device, wherein the processing unit is operable to operate the alert device to create the alert in response to an electronic communication from the occupancy sensor.

2. The case of claim 1, wherein the processing unit operates the alert device after the dental appliance is detected for a period of time.

3. The case of claim 1, further comprising a lid sensor, wherein the lid sensor is operable to detect if the lid is open.

4. The case of claim 1, wherein the processing unit operates the alert device after the lid has not been opened for a period of time.

5. The case of claim 1, further comprising a wireless charging receiver in electrical communication with the power source.

6. A dental appliance case for receiving a dental appliance, the case comprising:
   a lid;
   a base having an open cavity that is able to at least partially receive a dental appliance, wherein the base and lid are operable to be temporarily aligned and brought together, forming a closed cavity between the lid and base that is able to receive the dental appliance;
   a power source;
   an occupancy sensor, wherein the occupancy sensor is operable to detect the presence of the dental appliance in the open cavity regardless of whether the lid and base are brought together;
   a communication array, wherein the communication array is operable to send and receive wireless communications; and,
   a processing unit in electrical communication with the power source, occupancy sensor, and the communication array, wherein the processing unit is operable to operate the communication array to send wireless communications describing the presence of the dental appliance in the open and/or closed cavity.

7. The case of claim 6, wherein the processing unit operates the communication array after the dental appliance is detected in the open and/or closed cavity for a period of time.

8. The case of claim 6, further comprising an alert device operable to create an alert, wherein the alert device is selected from the group consisting of a sound device, a vibration device, and a light emitting device.

9. The case of claim 8, wherein the processing unit operates the alert device after the dental appliance is detected in the open and/or closed cavity for a period of time.

10. The case of claim 8, wherein the processing unit operates the alert device after a wireless communication is received by the communications array.

11. The case of claim 8, further comprising a lid sensor, wherein the lid sensor is operable to detect if the lid is open.

12. The case of claim 11, wherein the processing unit operates the communications array after the lid has not been opened for a period of time.

13. The case of claim 11, wherein the processing unit operates the alert device after the lid has not been opened for a period of time.

14. The case of claim 6, further comprising a wireless charging receiver in electrical communication with the power source.

15. A dental appliance case, the case comprising:
- a cavity configured to receive a dental appliance;
- an electromagnetic wave emitter configured to output one or more wavelength;
- an electromagnetic wave receiver configured to detect one or more wavelength output by the electromagnetic wave emitter; and
- one or more processor configured to determine whether the dental appliance is within the cavity based on a change in the detection of the one or more wavelength by the electromagnetic wave receiver.

16. The case of claim 15, wherein the electromagnetic wave emitter is configured to output the one or more wavelength in the direction of the dental appliance, when the dental appliance is positioned within the cavity.

17. The case of claim 15, wherein the dental appliance is primarily made of an optically translucent or transparent material; and
- wherein the one or more wavelength output by the electromagnetic emitter is at least partially absorbed and/or reflected by the dental appliance.

18. The case of claim 15, wherein a least a portion of the dental appliance is positioned between the electromagnetic wave emitter and the electromagnetic wave receiver when the dental appliance is within the cavity.

19. The case of claim 15, wherein one or more wavelength output by the electromagnetic wave emitter is within an infrared region.

20. The case of claim 15, wherein one or more wavelength output by the electromagnetic wave emitter is within an ultraviolet region.

* * * * *